United States Patent
Perez

(10) Patent No.: US 12,197,049 B1
(45) Date of Patent: Jan. 14, 2025

(54) TUNNEL VISION MASK

(71) Applicant: Jerry Perez, Miami, FL (US)

(72) Inventor: Jerry Perez, Miami, FL (US)

( * ) Notice: Subject to any disclaimer, the term of this patent is extended or adjusted under 35 U.S.C. 154(b) by 1092 days.

(21) Appl. No.: 17/091,423

(22) Filed: Nov. 6, 2020

(51) Int. Cl.
  *G02C 7/16* (2006.01)
  *A61M 21/00* (2006.01)

(52) U.S. Cl.
  CPC ............... *G02C 7/16* (2013.01); *A61M 21/00* (2013.01); *A61M 2021/0044* (2013.01)

(58) Field of Classification Search
  CPC ... G02C 7/16; G02C 5/001–005; G02C 11/12
  See application file for complete search history.

(56) References Cited

U.S. PATENT DOCUMENTS

| | | | | |
|---|---|---|---|---|
| 4,059,347 A * | 11/1977 | Eitel | ........................ | G02C 7/16 33/262 |
| 4,292,030 A * | 9/1981 | Lobdell | .................. | G09B 19/00 434/262 |
| 4,452,516 A * | 6/1984 | Salia-Munoz | ..... | G02B 27/0025 351/45 |
| 4,602,856 A * | 7/1986 | Marks | ....................... | G02C 7/16 351/44 |
| 5,682,219 A * | 10/1997 | Kim | ........................ | A61F 9/045 351/44 |
| 2010/0259716 A1* | 10/2010 | Kusmec-Aguilar | ... | G02C 7/105 351/47 |
| 2016/0038711 A1* | 2/2016 | Perez | .................... | A61M 21/00 600/26 |
| 2017/0071793 A1* | 3/2017 | Sherer | ..................... | A61F 9/027 |
| 2019/0209044 A1* | 7/2019 | Hess | .................... | A61B 5/6898 |

\* cited by examiner

*Primary Examiner* — Thaddeus B Cox
(74) *Attorney, Agent, or Firm* — Christopher J. Vandam, PA; Chris Van Dam

(57) ABSTRACT

A treatment method for a user with attention deficit hyperactivity disorder, that includes the use of a mask to create a tunnel vision restriction for the user. Different sets of visual tasks are assigned to the user as he or she progress to reduce the number of distraction episodes. Depending on the progress the user experiences, the mask is removed, and the user is assigned initially the same tasks he or she undertook with the mask on. The steps are repeated to reduce the number of distracting episodes experienced by the user and increasing the complexity and completion time of the tasks.

4 Claims, 2 Drawing Sheets

TUNNEL VISION MASK

BACKGROUND OF THE INVENTION

1. Field of the Invention

The present invention relates to a tunnel vision therapeutic method for treating users with learning disabilities to become more attentive and improve the focus and learning ability of the user.

2. Description of the Related Art

Children with ADD (Attention Deficit Disorder) or ADHD (Attention Deficit Hyperactivity Disorder) have more difficulties than normal children in activities that require concentration. These conditions are treatable. The condition affects also adults. It is estimated that nearly 17 million American are affected by ADHD.

Several treatment methods have been used in the past. None of them, however, include the use of a mask that forces the user to concentrate his/her attention to a pre-defined area, over a predetermined period of time, with calibrated complexity and challenges on the targeted material. The user becomes familiar with the mask initially and as it is required to engage in certain activities (i.e. games, etc.) that require concentration, his/her visual tunnel is restricted. Eventually, the mask is used for increasing periods of time depending on the progress achieved.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a treatment method with a restricted tunnel vision that helps users with learning disabilities.

It is another object of this invention to provide a tunnel vision treatment method that helps to condition users to become more attentive and concentrated.

It is still another object of the present invention to provide a tunnel vision method that helps to minimize distractions in a learning environment to users with learning disabilities to help improve the focus and learning ability of the users.

It is also another object of the present invention to provide a tunnel vision method that can be used with multiple users simultaneously.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
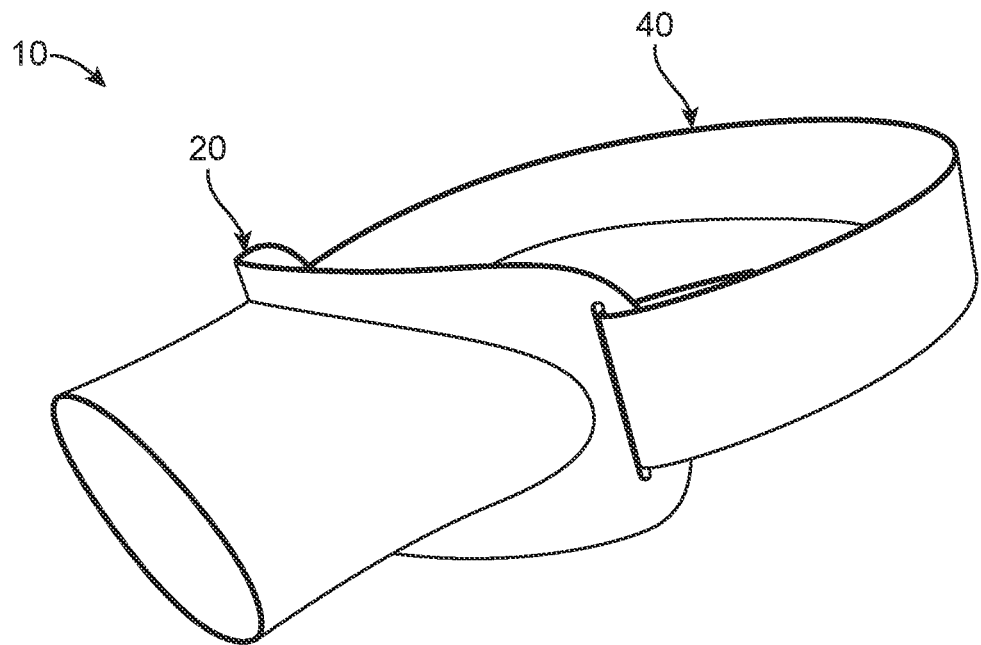
FIG. 1 represents an isometric inclined view of an embodiment for the mask subject of the present invention.
Figure 2:
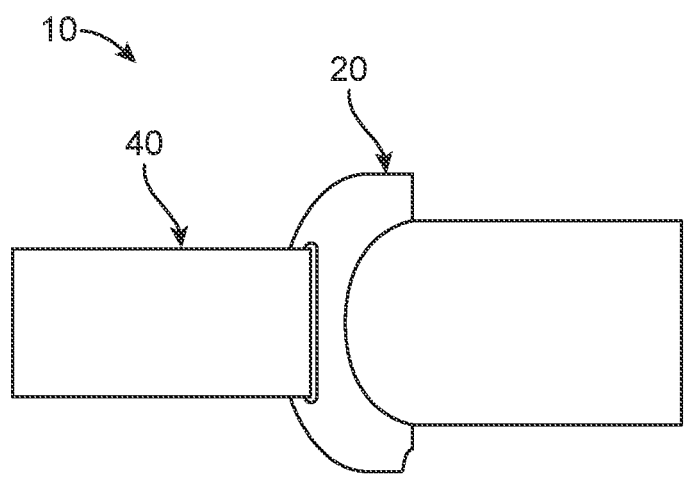
FIG. 2 shows an elevational side view of the mask shown in FIG. 1.
Figure 3:
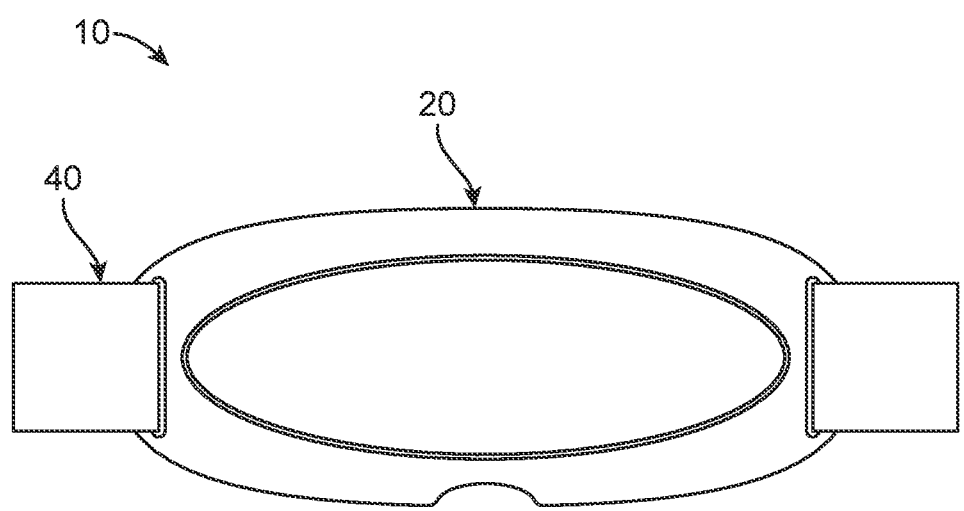
FIG. 3 illustrates a rear elevational view of the mask shown in the previous figures.

The method subject of the present application includes the use of a mask to create a restricted tunnel vision for the users. Initially, the user is shown the mask 10 and allowed to familiarize himself or herself with the physical characteristics of the object. After trying the mask on without using the straps 40, the user gets used to having the mask against his or her face for increasing periods of time. The person coordinating the treatment method, coordinator, observes the user and helps overcome any physical problems that a user may encounter with the mask. Then, the straps are used to keep the mask on the user's face. The coordinator then selects a visual task for the user, such as a puzzle, game, or the like. Initially, the simplest tasks are assigned. The user is asked to do the puzzle or play the game with the mask on. For the purposes of this application, visual activities will refer to activities or tasks that require visual attention by the user to perform them. The performance may involve different movements or actions from a user, including selecting objects, writing, talking, etc. The time period for finishing the visual activities will be referred to as completion time. The complexity of the visual activities will vary in a calibrated manner from one set of visual activities to the next.

The objective is to avoid any distraction for increasing periods of time. Once the user is able to start and finish the tasks with the mask on, the same tasks are assigned without the mask. Then, additional tasks, with more complexity, such as writing and math exercises, are added. The period of time to execute the more complex tasks is increased in a calibrated manner and the student's progress is recorded.

Referring now to the drawings, where the mask used in the present invention is generally referred to with numeral 10, it can be observed that it basically includes a frame 20 and strap 40.

Frame 20 has, in one of the embodiments, an elliptical cross-section and extends longitudinally a distance L. In combination with distance L that extends a predetermined distance to provide a tunnel vision that forces a user to concentrate.

The method includes the following steps:
A) familiarizing the user with a mask having a frame with a substantially elliptical cross-section to create a tunnel vision restriction for the user.
B) The mask is brought against the user's face temporarily and allowed sufficient time for the user to get used to having the mask against his or her face. The mask is provided with straps for removably mounting the mask on the user's face after sufficient familiarization time with the mask has elapsed.
C) The mask is mounted to the user's face and the user is observed for a predetermined period of time. If necessary, the mask straps are adjusted.
D) A first set of simple visual activities that require the user's concentration and finishing each of said visual activities are assigned to the user.
E) After the assigned visual activities with the mask on are finished, the time required for completion is recorded. If necessary, the first simple task is repeated until a predetermined minimum time for completion is achieved.

F) The user is now asked to complete the simple first set of visual activities without the mask. The time to complete the first set of simple activities is recorded and, if the time taken to complete is not less than a predetermined minimum completion time, the user is asked to repeat the tasks assigned.

G) A second set of visual activities different than the first set of activities is assigned to the user. This second set is more complex than the first set requiring more concentration from the user. If the user cannot complete the second set of visual activities without the mask, the mask will then be used to prevent distractions and provide the necessary tunnel vision. Once the second set of visual activities is completed by the user within a predetermined time period, the same second set of visual activities are assigned without the mask. After completing the second set of visual activities without the mask within a predetermined time period, the user is ready to practice with a third set of visual activities.

H) Additional sets of visual activities are assigned with increasing degrees of complexity and requiring increasing time periods of the user's attention.

The progress of the user is recorded by including the dates of the exercises, time of completion and the sets of visual activities completed as well as the number of times they had to be repeated.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A treatment method for a user with attention deficit hyperactivity disorder, comprising the steps of:

A) familiarizing the user with a mask having a frame with an elliptical cross-section to create a tunnel vision restriction for the user and further including straps for removably mounting the mask on the user's face;
B) mounting the mask on the user's face, without using the straps, and allowing sufficient time for the user to get used to having the mask against his or her face;
C) mounting the mask to the user's face with the straps;
D) starting the user, with the mask on, on a first set of visual activities that require the user's concentration;
E) finishing the assigned first set of visual activities with the mask on;
F) starting the user, without the mask, on said first set of visual activities, and finishing each activity of said first set of visual activities;
G) assigning a second set of visual activities more complex than said first set of activities; and
H) repeating steps D through G wherein the second set of visual activities is to be completed with the user wearing the mask, then completed again with the user not wearing the mask, and then, for additional sets of visual activities that are iteratively/incrementally more complex than the second set of visual activities, the user will complete each additional set of visual activities first while wearing the mask and then again while not wearing the mask.

2. The treatment method set forth in claim 1, further comprising the step of recording a date for an assignment and execution of each of the sets of visual activities.

3. The treatment method set forth in claim 2 further comprising the step of recording a completion time for each of the sets of visual activities performed and completed within predetermined completion times by the user.

4. The treatment method set forth in claim 3 wherein each subsequent set of visual activities is designed with calibrated increments of complexity and completion times.

* * * * *